(12) United States Patent
Korkuch (10) Patent No.: US 12,121,681 B2
(45) Date of Patent: *Oct. 22, 2024

(54) GUIDEWIRE ACCESS SLEEVE

(71) Applicant: ABIOMED, Inc., Danvers, MA (US)

(72) Inventor: Christopher Nason Korkuch, Beverly, MA (US)

(73) Assignee: ABIOMED, INC., Danvers, MA (US)

( * ) Notice: Subject to any disclaimer, the term of this patent is extended or adjusted under 35 U.S.C. 154(b) by 899 days.

This patent is subject to a terminal disclaimer.

(21) Appl. No.: 17/182,332

(22) Filed: Feb. 23, 2021

(65) Prior Publication Data

US 2021/0252259 A1 Aug. 19, 2021

Related U.S. Application Data

(63) Continuation of application No. 16/021,853, filed on Jun. 28, 2018, now Pat. No. 10,953,205.

(Continued)

(51) Int. Cl.
*A61M 25/09* (2006.01)
*A61M 25/06* (2006.01)
(Continued)

(52) U.S. Cl.
CPC .. *A61M 25/09041* (2013.01); *A61M 25/0662* (2013.01); *A61M 25/0668* (2013.01);
(Continued)

(58) Field of Classification Search
CPC ........ A61M 25/09041; A61M 25/0662; A61M 25/0668; A61M 60/148;
(Continued)

(56) References Cited

U.S. PATENT DOCUMENTS 6,183,443 B1 2/2001 Kratoska et al.
6,579,264 B1 6/2003 Rossi
(Continued)

FOREIGN PATENT DOCUMENTS

GB 2033236 A 5/1980
JP 2003180698 A 7/2003
(Continued)

OTHER PUBLICATIONS

Office Action from corresponding Korean Patent Application No. 10-2020-7002227 dated Mar. 14, 2023 (16 pp.).
(Continued)

*Primary Examiner* — Amber R Stiles
(74) *Attorney, Agent, or Firm* — Botos Churchill IP Law LLP (57) ABSTRACT

An access sleeve can be attached to a medical device having first and second ends, the first end being positioned inside of a patient and the second end being positioned external to a patient. The access sleeve can include a tubular sleeve body having first and second open ends that define a first lumen extending along a longitudinal axis of the sleeve body. An opening in the sleeve body can connect the first lumen to an outer surface of the sleeve body. The access sleeve can be selectively attached to the medical device (e.g., catheter of a heart pump) and inserted into the access site when the medical device is positioned in the patient. The access sleeve can maintain vascular access to a patient's access site such as an arteriotomy and can be removed without disturbing the position of the medical device.

24 Claims, 10 Drawing Sheets

Related U.S. Application Data (60) Provisional application No. 62/525,779, filed on Jun. 28, 2017.

(51) Int. Cl.
*A61B 17/00* (2006.01)
*A61B 90/00* (2016.01)
*A61M 60/148* (2021.01)

(52) U.S. Cl.
CPC .............. *A61B 2017/00336* (2013.01); *A61B 2017/00778* (2013.01); *A61B 2090/064* (2016.02); *A61M 2025/0681* (2013.01); *A61M 2025/09091* (2013.01); *A61M 2025/09175* (2013.01); *A61M 60/148* (2021.01); *A61M 2210/125* (2013.01)

(58) Field of Classification Search
CPC .......... A61M 2025/0681; A61M 2025/09091; A61M 2025/09175; A61M 2210/125; A61B 2017/00336; A61B 2017/00778; A61B 2090/064
See application file for complete search history.

(56) References Cited

U.S. PATENT DOCUMENTS

| | | | |
|---|---|---|---|
| 10,953,205 B2 * | 3/2021 | Korkuch | A61M 25/0668 |
| 2001/0031979 A1 * | 10/2001 | Ricci | A61F 2/97 606/194 |
| 2002/0032432 A1 | 3/2002 | Nash et al. | |
| 2002/0072712 A1 | 6/2002 | Nool et al. | |
| 2003/0032941 A1 | 2/2003 | Boyle et al. | |
| 2003/0212373 A1 | 11/2003 | Hall et al. | |
| 2004/0030319 A1 | 2/2004 | Korkor et al. | |
| 2008/0015625 A1 | 1/2008 | Ventura et al. | |
| 2009/0198309 A1 | 8/2009 | Gowda et al. | |
| 2012/0296409 A1 | 11/2012 | Kawakita | |
| 2014/0171736 A1 | 6/2014 | Stigall et al. | |
| 2014/0275795 A1 | 9/2014 | Little et al. | |
| 2016/0367786 A1 | 12/2016 | Mallin | |
| 2017/0049947 A1 | 2/2017 | Corbett et al. | |

FOREIGN PATENT DOCUMENTS

| | | |
|---|---|---|
| JP | 2005000553 A | 1/2005 |
| JP | 2016502879 A | 2/2016 |
| WO | 2007044907 A2 | 4/2007 |
| WO | 2011081007 A1 | 7/2011 |
| WO | 2011109307 A1 | 9/2011 |
| WO | 2017031243 A1 | 2/2017 |

OTHER PUBLICATIONS

Office Action from corresponding Japanese Application No. 2019-572501 mailed Apr. 20, 2022 (10 pages).

Office Action from corresponding Australian Patent Application No. 2018294227 dated May 18, 2023 (5 pp.).

Office Action from corresponding Indian Patent Application No. 202017001793 dated Dec. 13, 2022 (4 pp.).

International Search Report, PCT/US2018/040079, dated Oct. 9, 2018.

International Search Report, PCT/US2018/040079, dated Feb. 6, 2019.

Office Action dated Jun. 5, 2024 for Japanese Patent Application No. 2023-138859 (7 pp.).

* cited by examiner

GUIDEWIRE ACCESS SLEEVE

CROSS-REFERENCE TO RELATED APPLICATIONS

This application is a continuation of U.S. application Ser. No. 16/021,853, filed Jun. 28, 2018, and published as US 2019/0001103 A1, which claims priority to U.S. Provisional Application Ser. No. 62/525,779, filed Jun. 28, 2017, the disclosures of which are hereby incorporated by reference in their entireties.

BACKGROUND

A medical device, such as an intravascular heart pump assembly, can be introduced into a patient in various ways. In general, a heart pump can pump blood from the heart into a vessel to provide hemodynamic support. When deployed in the left side of the heart, a heart pump assembly pumps blood from the left ventricle of the heart and expels blood into the aorta. When deployed in the right side of the heart pumps blood from the inferior vena cava, bypasses the right atrium and right ventricle, and expels blood into the pulmonary artery.

Heart pump assemblies are introduced surgically or percutaneously during a cardiac procedure through the vascular system. In one common approach, pump assemblies are inserted by a catheterization procedure through the femoral artery using a sleeve, such as a peel-away introducer sleeve. The peel-away introducer sleeve can be inserted into the femoral artery through an arteriotomy to create an insertion path for the pump assembly. A portion of the pump assembly is then advanced through an inner lumen of the introducer and into the artery. Once the pump assembly has been inserted, the peel-away introducer sleeve is peeled away. A repositioning sleeve can then be advanced over the pump assembly and into the arteriotomy.

In the event that the pump needs to be removed and/or replaced, the peel away introducer sleeve can maintain access to the arterial access site and guidewires or other devices can be inserted through the valve disposed in the hub of the introducer. After the pump is inserted, the introducer sleeve is removed (e.g., peeled away) to make way for the repositioning sleeve. The repositioning sleeve does not include a valve or pathway for inserting devices into the vessel. Accordingly, if the pump needed to be removed or repositioned, then this requires another access procedure (i.e., create an arteriotomy and insert another introducer sleeve) to continue the planned interventional procedure. For short term procedures, performing another access procedure would require more steps, take additional time, and increase the cost of the procedure.

SUMMARY OF INVENTION

Systems, devices and methods for access to a medical device are presented. An access sleeve provides a means for maintaining access to a vessel during use of a repositioning sleeve or removal of a medical device. The access sleeve allows for attachment to the catheter of an indwelling pump, followed by insertion of the access sleeve into the vasculature of a patient by sliding along the catheter body of the pump while using the catheter body itself as a rail. The catheter can subsequently be removed leaving the access sleeve indwelling to maintain access to the vessel of interest. Alternatively, a guidewire can be introduced using the indwelling access sleeve prior to catheter removal to maintain access to an arterial site, after which the catheter and pump can be removed. In certain configurations, once a guidewire is employed even the access sleeve can be removed.

The access sleeve therefore provides an in-line means to attach to a medical device without requiring access to the ends of the medical device. Instead, when the medical device is in the vasculature of the patient, the access sleeve attaches to a portion of the medical device that is external to the vessel. The access sleeve is then positioned in the vessel of interest by sliding into place using the catheter body of the medical device as a guide. Once in place, the access sleeve maintains access to the vessel and the medical device can be removed or repositioned as necessary. By not requiring access to the ends of the medical device, the access sleeve can be easily integrated with many operating procedures where access to a site within a patient is necessary, thereby doing away with the need for additional access steps during an intervention procedure.

According to an implementation of the present disclosure, there is provided an access sleeve for attachment to a medical device. The access sleeve comprises a tubular sleeve body extending along a longitudinal axis of the access sleeve, the sleeve body having first and second open ends. The access sleeve further comprises a first lumen extending along the longitudinal axis between the first and second open ends of the sleeve body. The access sleeve also comprises a lateral opening in the sleeve body connecting the first lumen to an outer surface of the sleeve body. Here the lateral opening of the access sleeve is configured to be selectively expanded to attach the access sleeve to a medical device.

In some implementation, the sleeve body comprises a second lumen extending along the longitudinal axis between the first and second open ends of the sleeve body, the second lumen being sized and shaped for passage of a guidewire. In other implementations, the opening extends linearly between the first and second open ends of the sleeve body and is parallel to the longitudinal axis of the first lumen of the sleeve body. In certain implementations, the opening extends in a helical spiral between the first and second open ends of the sleeve body. In some implementations, the sleeve comprises an inner surface fabricated with an irregular geometry to minimize contact between the sleeve body and the medical device. In other implementations, the inner surface comprises at least one recess extending between the first and second open ends of the tubular sleeve body.

In certain implementations, the access sleeve further comprises a hub attached to the second open end of the tubular sleeve body. In other implementations, the access sleeve further comprises a tip at the first open end of the tubular sleeve body, the tip having inner surface defining a tip lumen that extends between proximal and distal ends of the tip, the tip lumen being in fluid communication with the first lumen of the sleeve body. In some implementations, an outer diameter of the proximal end of the tip is larger than an outer diameter of the distal end of the tip such that the tip is tapered along its proximal-to-distal length. In other implementations, a diameter of the inner surface at the proximal end of the tip is larger than a diameter of the inner surface of the tip at the distal end.

In certain implementations, a diameter of the inner surface at the proximal end of the tip is equal to a diameter of the inner surface at the distal end of the tip. In other implementations, sleeve body comprises a first material and the tip comprises a second material. In some implementations, the first material is substantially stiffer than the second material, and the second material is substantially more elastic than the first material. In other implementations, the first material comprises at least one of: high-density polyethylene (HDPE) material, a medium-density polyethylene (MDPE) material, a low-density polyethylene (LDPE) material, a polyether block amide (such as PEBA), a material with an elastic modulus of about 81-307 MPa, and a material with a yield strain of 20-30%. In certain implementations, the second material comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%. In other implementations, the hub any one of a high-density polyethylene (HDPE) material, a medium-density polyethylene (MDPE) material, a low-density polyethylene (LDPE) material, polyether ether ketone (PEEK), and a polyether block amide (such as PEBA).

According to another implementation of the present disclosure there is provided an access system. The access system comprises a medical device configured for insertion into an arteriotomy of a patient, the medical device having a first end and a second end. The access system also comprises an access sleeve. The access sleeve comprises a tubular sleeve body extending along a longitudinal axis, the sleeve body having first and second open ends. The access sleeve also comprises a first lumen extending along the longitudinal axis between the first and second open ends of the sleeve body. The access sleeve further comprises a lateral opening in the sleeve body connecting the first lumen to an outer surface of the sleeve body, the lateral opening comprising a slit that extends along the length of the sleeve body. Here the access sleeve is configured to be selectively expanded to attach the access sleeve to the medical device such that the medical device is positioned in the first lumen and the first lumen allows for the passage of at least the medical device.

In some implementations, the access sleeve body has a cross-sectional shape that is substantially C-shaped. In certain implementations, the medical device includes a catheter onto which the access sleeve attaches. In some implementations, the access sleeve is configured to slide distally along the catheter and be advanced into the arteriotomy while still attached to the catheter. In other implementations, the sleeve further comprises a second lumen extending along the longitudinal axis between the first and second open ends of the sleeve body for passage of a guidewire. In some implementations, the sleeve comprises an inner surface having an irregular geometry to minimize contact between the sleeve body and the medical device. In certain implementations, the inner surface comprises at least one recess extending between the first and second open ends of the tubular sleeve body. In some implementations, the access system further comprises a hub attached to the second open end of the tubular sleeve body.

According to a further implementation of the present disclosure there is provided a method of attaching an access sleeve to a medical device positioned within a vascular site of a patient such that the medical device comprises a first section positioned within the vasculature and a second section positioned external to the patient. The method comprises attaching the access sleeve to the second portion of the medical device via a first lumen. The method also comprises positioning the access sleeve within the vasculature by sliding the access sleeve along the medical device where the medical device serves as a rail for guiding the access sleeve such that the access sleeve is in the proximity of the first portion of the medical device when positioned within the vasculature. The method finally involves removing the medical device.

In some implementations, the access sleeve further comprises a second lumen with a stylet, and the method further comprises removing the stylet from the second lumen once the access sleeve is positioned within the vasculature. In other implementations, the method further comprises removing the access sleeve while maintaining the position of the guidewire in the vasculature. In certain implementations, the method also comprises removing the medical device from the vascular site. In some implementations, the method further comprises removing the access sleeve while maintaining the position of the guidewire in the vasculature, and removing the medical device from the vascular site.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices described herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of medical devices such as transcatheter aortic valve replacement (TAVR) delivery systems, cardiac therapy and cardiac assist devices, including balloon pumps, cardiac assist devices implanted using a surgical incision, and the like.

The systems, methods and devices described herein provide an access sleeve for attachment to a medical device (such as a percutaneous heart pump) after the device has been inserted into a blood vessel through a vessel aperture, i.e., an indwelling medical device. The access sleeve comprises a tubular sleeve body extending along a longitudinal axis, where the sleeve body has a first open end and a second open end. The access sleeve also comprises an opening in the sleeve body connecting the first lumen to an outer surface of the sleeve body. The access sleeve is configured to be attached to the medical device without requiring access to the first end or the second end of the medical device such that vascular access to a patient is maintained by the access sleeve after removal of the medical device. In certain implementations, the sleeve body may comprise a second lumen for a guidewire.

The opening in the sleeve body allows for the access sleeve to be attached in-line to a medical device without requiring access to the ends of the medical device. With this configuration, the medical device does not need to be threaded through the access sleeve thereby making the device adaptable to a host of medical devices. Further, the sleeve is made of a flexible material which means that the arms of the sleeve can flex out of the way for attachment to medical devices of varying diameters, and can return to their original shape after the medical device is removed. This enables the sleeve to slide along the medical device while remaining attached to the device. This also allows for the passage of a medical device with cross-sections having diameters that are larger than that of the first lumen of the access sleeve for the purpose of removal of the medical device from the vasculature of a patient. The resilience of the arms of the access sleeve also minimizes the formation of cavities between the sleeve body and the medical device. This reduces the likelihood of fluid and blood being trapped in such cavities which can lead to unwanted haemostasis and coagulation in the first lumen.

Figure 1:
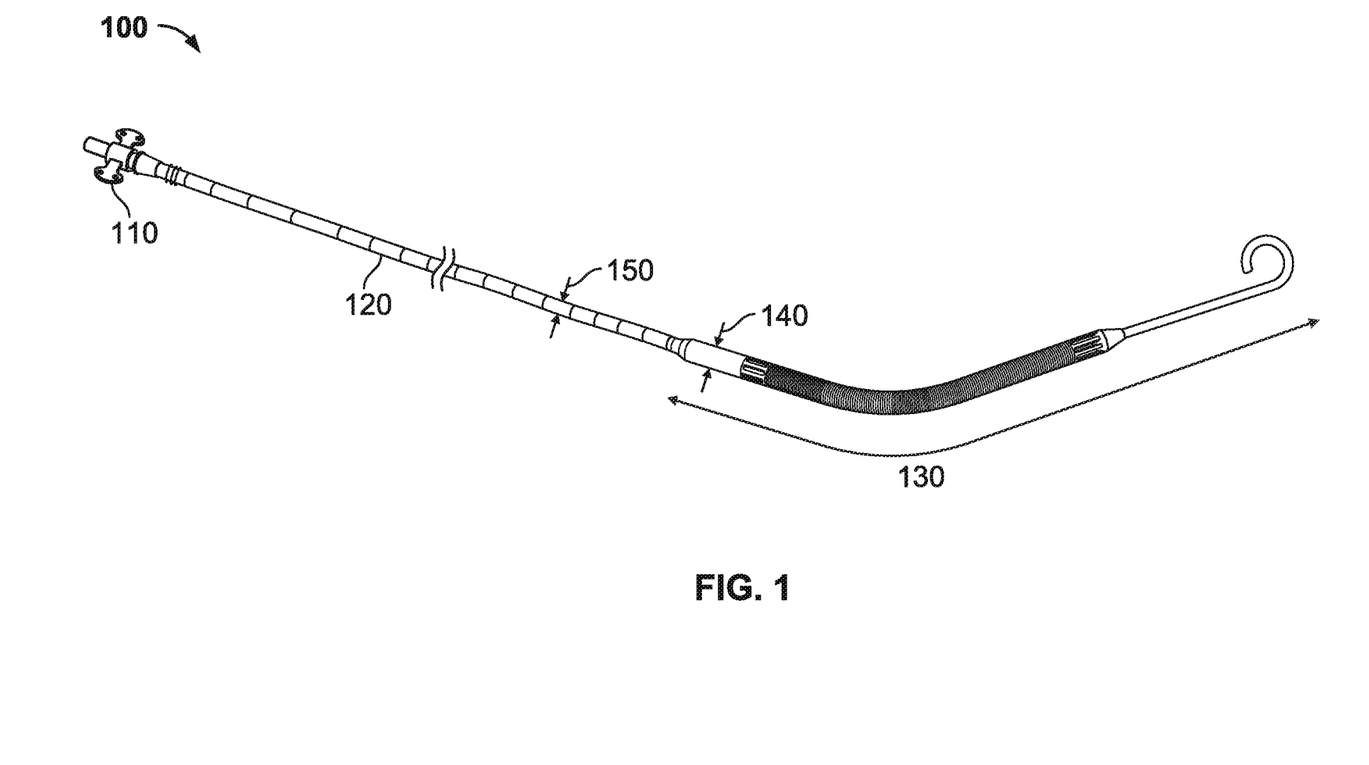
FIG. 1 shows an isometric view of an illustrative prior art medical device.

FIG. 1 shows an illustrative medical device such as a percutaneous pump 100 according to certain implementations. The pump 100 comprises a pump handle 110, a pump head 130, a catheter 120 connecting the pump handle 110 to the pump head 130, and a connecting hub 160. The catheter 120 is tubular and has a substantially uniform outer diameter 150. The catheter 120 enables the pump head 130 and the pump handle 110 to be in electro-mechanical communication. The pump handle 110 is in communication with control circuitry which allows the control of the pump head 130. The pump head 130 contains electro-mechanical components that enable the device to perform various tasks within the body of a patient, such as pump blood from a location within the body. The pump head 130 has a diameter 140 that is larger than the diameter 150 of the catheter 120. An example of such a percutaneous pump is the Impella 2.5™ system (Abiomed, Inc., Danvers, Massachusetts). It will be understood that while a percutaneous heart pump is described herein, any other percutaneous medical device can be used in conjunction with the present disclosure.

Figure 2:
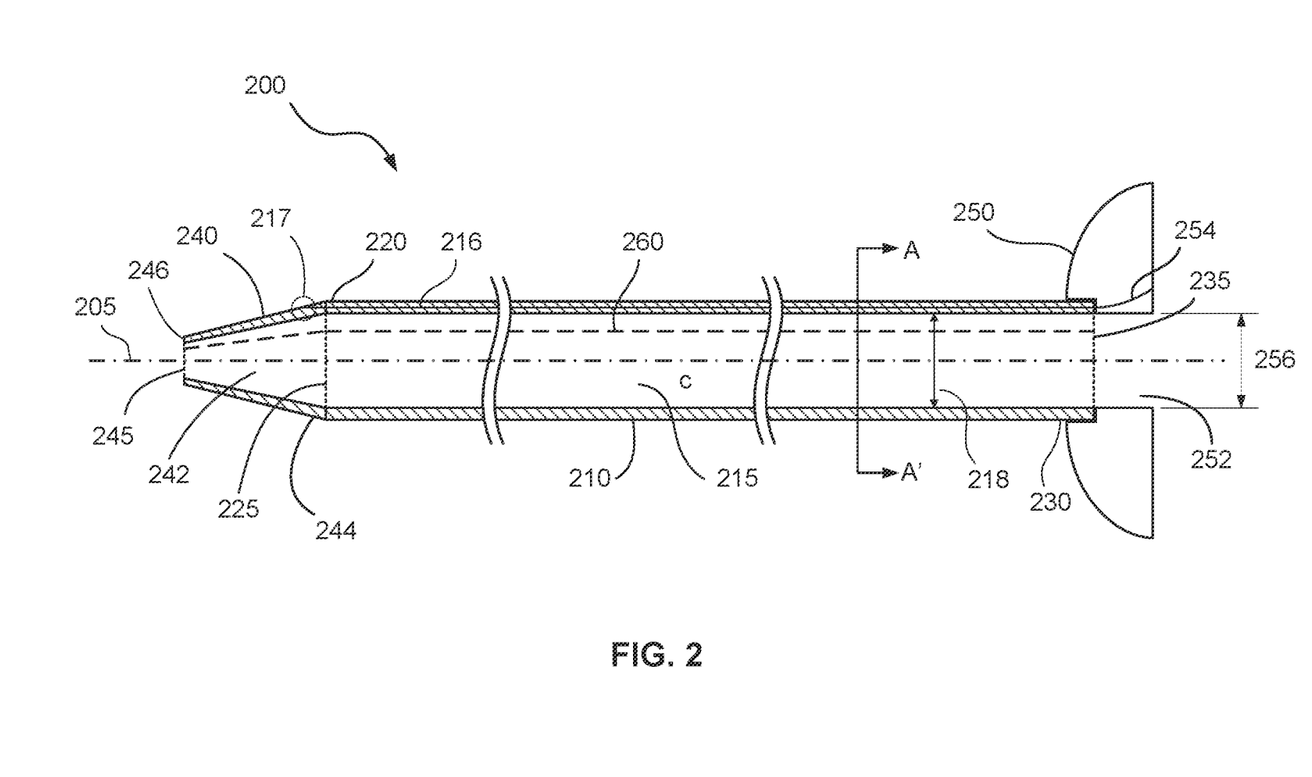
FIG. 2 shows a longitudinal cross section of an access sleeve according to an implementation of the present disclosure.

FIG. 2 shows a cross sectional view of an illustrative access sleeve 200 according to certain implementations of the present disclosure. The access sleeve 200 comprises a sleeve body 210 having a longitudinal axis 205. The sleeve body 210 forms a lumen 215 between a distal end 220 and a proximal end 230. The sleeve body 210 (and hence the lumen 215) has an internal diameter 218. The distal end 220 has an open end 225 and the proximal end 230 has an open end 235, thereby defining an inner surface and an outer surface. The lumen 215 provides a passageway for a medical device, such as the percutaneous pump 100 of FIG. 1. In some implementations, the access sleeve 200 may have more than one lumen 215. For example, the access sleeve 200 may have two lumens, a lumen 215 for the passage of an indwelling catheter 120 of a medical device 100, and the other, a peripheral lumen 216, for the passage of a guidewire. In certain implementations, the sleeve body 210 may be tubular. In other implementations, a flexible tip 240 having an internal lumen 242 and an open distal end 245 is attached to the distal end 220 of the sleeve body 210. In this manner the lumen 215 of the sleeve body 210 is in fluid communication with the lumen 242 of the tip 240 such that a continuous passageway is formed from the proximal open end 235 of the sleeve body 210 to the distal open end 245 of the tip 240. Additionally, the peripheral lumen 216 terminates in the tip 240 at lateral opening 217. In some implementations, the tip 240 is integrally formed with the tubular sleeve body 210. In certain implementations, the access sleeve 200 comprises an opening 260 extending longitudinally along the sleeve body 210. The opening 260 connects the lumen 215 to the outer surface of the sleeve body 210 such that the cross-section of the access sleeve 200 is substantially C-shaped. In certain implementations, the opening 260 comprises a slit running down the entire length of the sleeve 200. In certain implementations, the access sleeve 200 may also comprise a hub 250 that is coupled to the proximal end 230 of the sleeve body 210 to allow the proximal end 230 of the sleeve 200 to be secured to a patient. The hub 250 also facilitates insertion of a guidewire into the peripheral lumen 216 from the proximal end 230 of the access sleeve 200.

Figure 3:
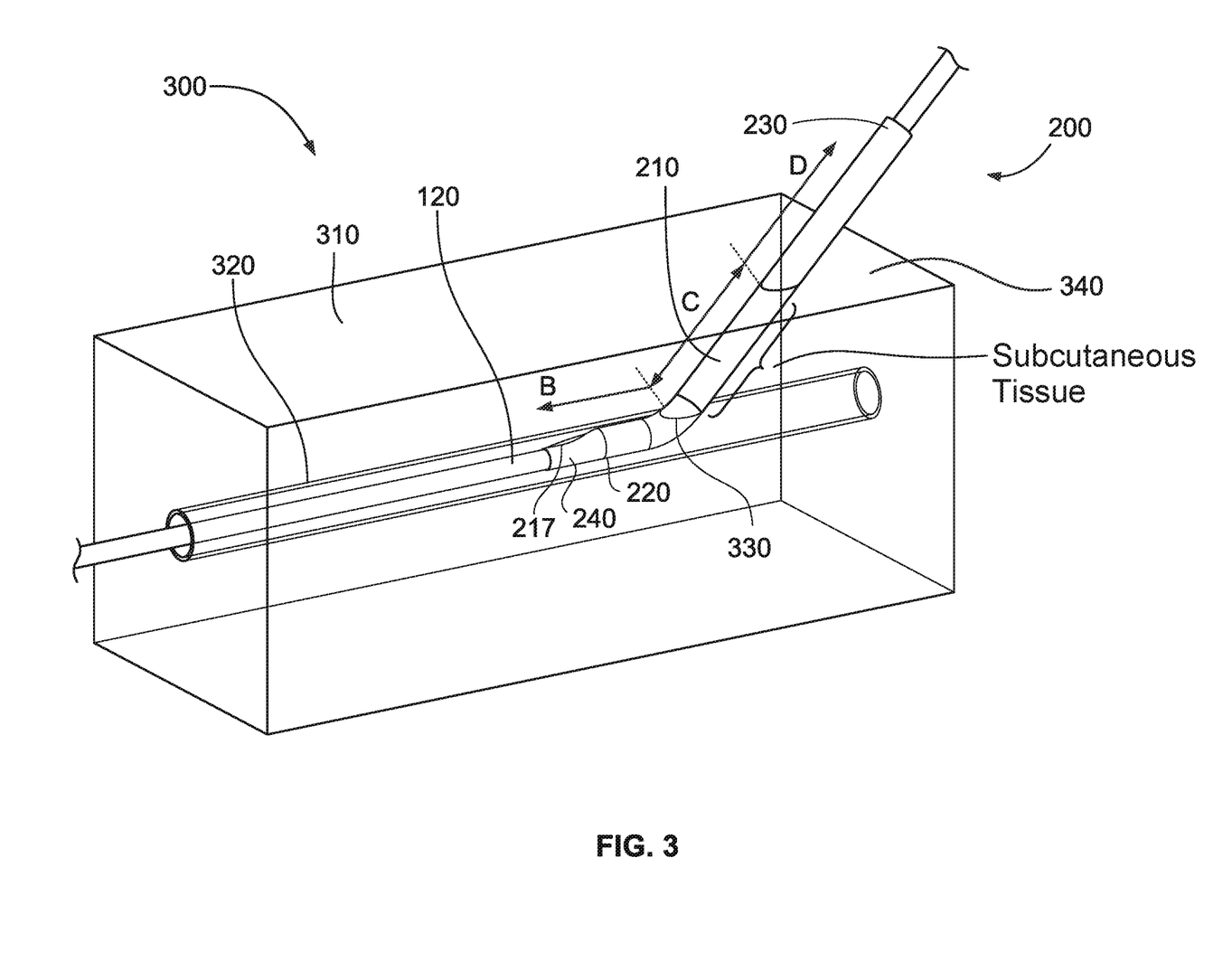
FIG. 3 shows an isometric view of the access sleeve of FIG. 2 attached to a medical device.

Attachment of the access sleeve 200 to a medical device, such as the percutaneous pump 100 shown in FIG. 1, will now be described with respect to FIG. 3. FIG. 3 shows representative tissue of a patient comprising of an artery 320, subcutaneous tissue 310, and a skin layer 340 where the pump 100 has been inserted into the vasculature of a patient, such as a blood vessel as depicted in the figure (only the indwelling catheter 120 of the pump 100 is shown in the figure). The pump 100 may have been introduced into the vasculature 320 of the patient via an arteriotomy 330 using known techniques. As mentioned, the catheter 120 provides the necessary fluid and electro-mechanical connections between the pump head to the pump handle 110. Thus, when the pump head 130 is in position, a first portion of the catheter 120 would reside in the artery 320 of the patient, a second portion of the catheter would reside in the subcutaneous tissue 310, and a third portion of the catheter would be exterior to the patient tissue, i.e., external to the skin layer 340. In FIG. 3, the first portion is distal from the arteriotomy 330, as indicated by arrow B, the second portion is proximal to the arteriotomy 330, as indicated by arrow C, and the third portion is external to the tissue, as indicated by arrow D.

Once the medical device 100 has been used, it may be necessary to completely remove it from the vasculature 320 to make way for another medical device. In accordance with implementations disclosed herein, access to the vasculature 320 can be maintained by the access sleeve 200 alone, by the access sleeve 200 with a guidewire, or with a guidewire after removal of the access sleeve 200, all of which require the attachment of the access sleeve 200 to the catheter body 120 of the medical device 100. Thus, in order to maintain access to the vasculature 320 while the medical device is removed or, the access sleeve 200 is attached to the catheter body 120 of the medical device and the sleeve is inserted into the vasculature 320 of the patient. In order to position the access sleeve 200 in the desired location, the sleeve is first attached to the portion of the indwelling catheter exterior to the tissue (indicated by arrow D in FIG. 3). This attachment is done via slit 260 that runs along the sleeve body 210 of the access sleeve 200. The slit 260 is opened with the application of a separating force to the distal tip 220 of the sleeve body 210. This may be done by a physician's fingers such that an opening is created sufficient to accommodate the third portion of the catheter body 120 of the medical device 100, i.e., the opening would have to be greater than the external diameter 150 of the catheter body 120. In alternate embodiments, attachment of the access sleeve 200 to the catheter body 120 is actioned by a press-fit where the access sleeve 200 is pressed onto a portion of the catheter body 120 exterior to the tissue, and the flexure of the catheter body 120 facilitates attachment of the remaining length of the access sleeve 200. This opening of the slit 260 is possible due to various factors, for example, the nature of the material used to fabricate the access sleeve 200, which will be discussed in the following sections, the geometry of the access sleeve 200, the cross-sectional shape of the access sleeve 200, the position of the slit 260 on the cross-section of the access sleeve 200, the slit width, etc. The sleeve body 210 of the access sleeve 200 is then pushed onto the third portion of the catheter body 120 via slit 260 until the catheter body 120 is located in lumen 215 of the sleeve body 210. Once this occurs, the remaining length of the access sleeve 200 is attached to the third portion of the catheter body 120 until the entire sleeve body 210 coaxially encompasses the catheter body 120. This can be achieved by applying a longitudinal force on the proximal end 230 of the sleeve body 210 until the entire sleeve body 210 slides into place on the catheter body 120. The access sleeve 200 can thus be attached in-line to the percutaneous pump 100 without having access to the end of the catheter 120, i.e., without having access to the pump head 130. This is also advantageous when a medical device, such as the percutaneous pump 100, does not have a lumen residing through it for the passage of guidewire.

The access sleeve 200 acts as a cuff around the catheter body 120 when it is fully attached to the catheter body 120. Once attached, the access sleeve 200 can then be positioned in the vasculature 320 of the patient by sliding it along the catheter body 120 from the third portion, through the second portion, and over the first portion, and in so doing the access sleeve 200 will be guided into the arteriotomy 330 by the catheter body 120. In this manner, the catheter body 120 effectively serves as a guide rail for longitudinally positioning the access sleeve 200 along the catheter body 120. Entry into the arteriotomy 330, while guided by the catheter body 120, is further aided by the atraumatic tip 240 attached to the distal end 220 of the sleeve body 210 of the access sleeve 200. Specific features of the tip 240 that enable this ease of positioning will be discussed in the following sections. Note that in the implementation depicted in FIG. 3, the access sleeve 200 has a peripheral lumen 216 (not shown) fabricated in the sleeve body 210 for the passage of a guidewire, for example. The peripheral lumen 216 terminates in the tapered region of the tip 240 at a lateral opening 217.

The access sleeve 200 comprises a rigid material, such as a high-density polyethylene (HDPE) material, a medium-density polyethylene (MDPE) material, a low-density polyethylene (LDPE) material, a polyether block amide (such as PEBA), a material with an elastic modulus of about 81-307 MPa, and a material with a yield strain of 20-30%.

Figure 4:
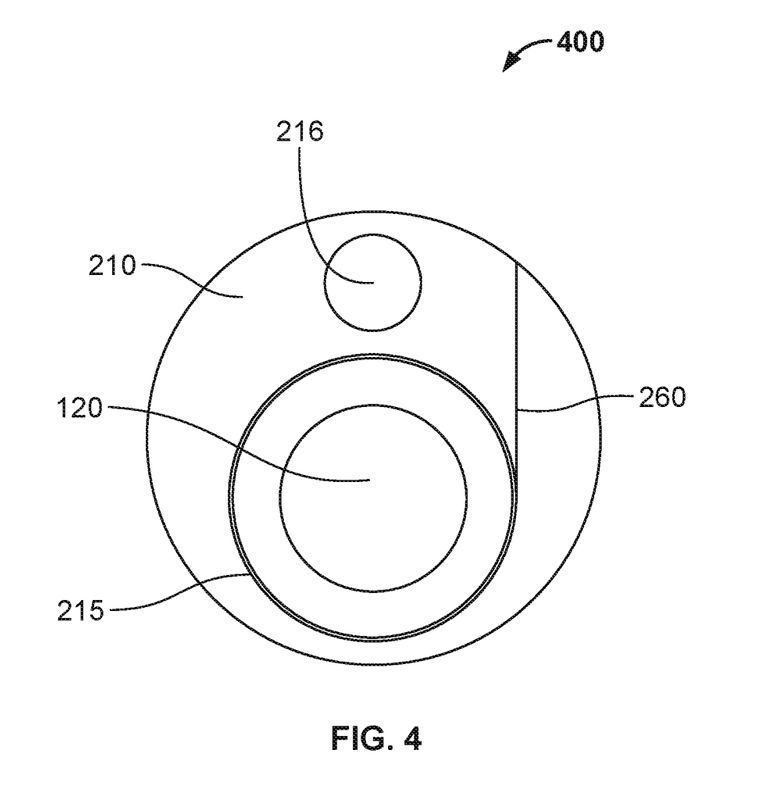
FIG. 4 shows a transverse cross section of the illustrative access sleeve of FIG. 2.

FIG. 4 shows a cross section of an access sleeve 400 taken along the section A-A' in FIG. 2. The access sleeve 400 has two lumens, a primary lumen 215 for attachment onto the catheter 120 of the medical device, as described in relation to FIG. 2, and a smaller peripheral lumen 216 for the passage of a guidewire, for example. The peripheral lumen 216 is fabricated within the walls of the sleeve body 210 and is distinct from the primary lumen 215. However, in certain implementations, the peripheral lumen 216 may be merged with the primary lumen 215 to form a track running alongside the primary lumen 215. While the peripheral lumen 216 is illustrated in FIG. 4 as having a circular cross section, it will be understood that the peripheral lumen 216 may be of any cross-sectional shape. The diameter 218 of the peripheral lumen 216 is smaller than that of the primary lumen 215. The primary lumen 215 has a diameter 218 that is substantially similar to the diameter 150 of the catheter body 120 such that the access sleeve 200 and the catheter body 120 have either a clearance fit or an interference fit while allowing longitudinal movement of the catheter body 120 with respect to the access sleeve 200. This seals the primary lumen 215 and minimizes (or even eliminates) the passage of fluid in any space that develops between the sleeve body 210 and the catheter body 120 during insertion which may coagulate and block the primary lumen 215 of the access sleeve 200. The diameter 218 of the primary lumen 215 is also smaller than that of the pump head 130. Thus, when it becomes necessary to completely remove the percutaneous pump 100 from the arteriotomy, the slit 260 allows for expansion of the access sleeve 200 and lumen 215 such that the pump head 130 is able to longitudinally move within the expanded lumen to be retrieved. After retrieval of the pump 100, the access sleeve returns to its original size. Such expansion and contraction of the sleeve 200 is also attributed to the flexible nature of the material used for the access sleeve 200.

Figure 5:
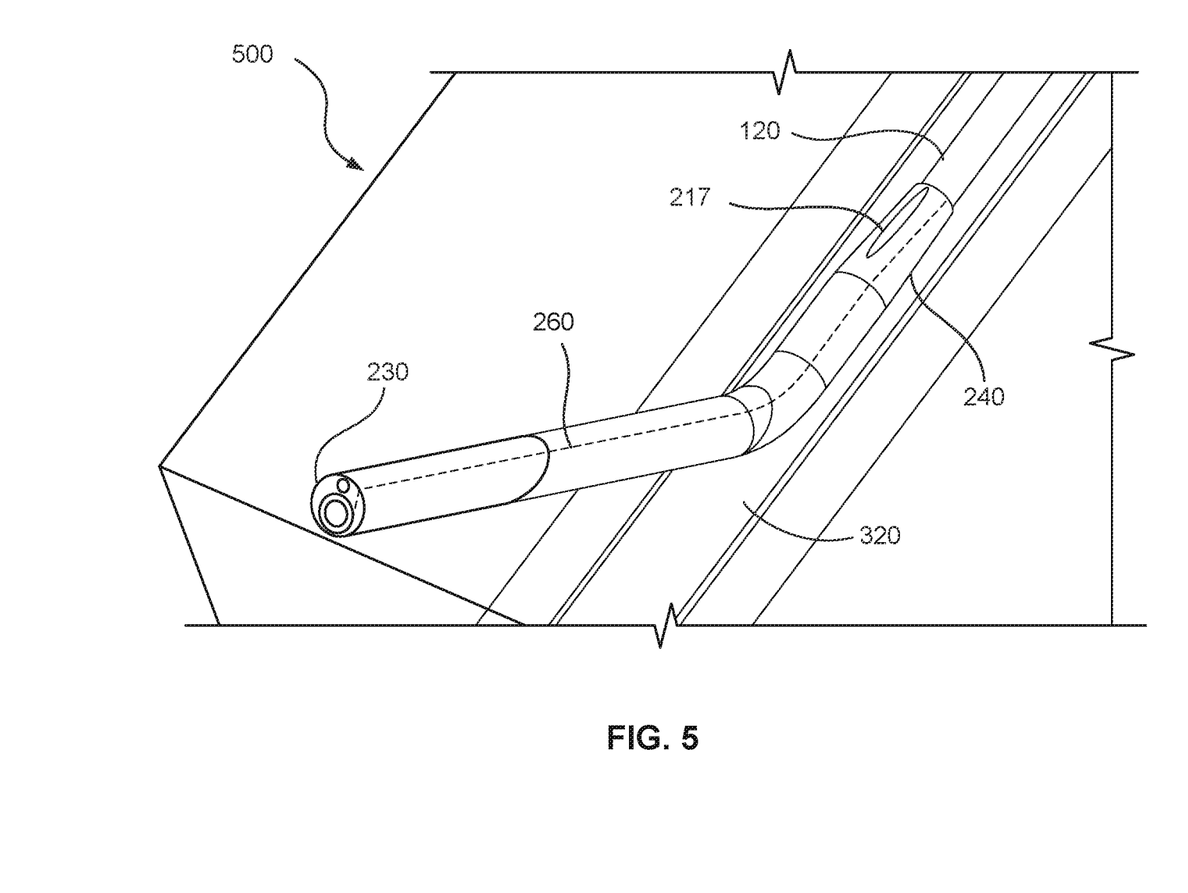
FIG. 5 shows an isometric view of a proximal portion of the access sleeve of FIG. 2 attached to the medical device of FIG. 1.

The slit 260 is fabricated as an opening in the sleeve body 210 and runs longitudinally along the length of the access sleeve 200. In certain implementations, the slit 260 is a linear cut line that runs parallel to the longitudinal axis 205 of the access sleeve 200, as illustrated in FIG. 5. Such a linear slit 260 simplifies fabrication of the access sleeve 200. In other implementations, the slit runs spirally with respect to the longitudinal axis 205 of the sleeve 200. Such a spiral slit 260 allows for a higher level of flexibility while improving the resistance of the access sleeve 200 to kink around bends once inserted into the arteriotomy of the patient. The spiral slit 260 in the access sleeve 200 also prevents detachment form the medical device. Additionally, the spiral slit 260 provides the access sleeve 200 with added strength.

In some implementations, the inner surface of the sleeve body 210 may have an irregular geometry to minimize contact with a medical device (e.g., medical device 100) that is advancing through the primary lumen 215. Such irregular geometry may include structures that span at least a portion of the longitudinal length of the sleeve body 210. Such structures may include ribs, projections, indentations, for example, that reduce the amount of contact the inner surface 204 of the sleeve body 210 makes with a medical device 100 that is advanced through the primary lumen 215. In one implementation, the inner surface 204 of the sleeve body 210 may be provided with at least one rib or projection that runs along at least a portion of the longitudinal length of the sleeve 210. Such structures may appear as raised features that protrude from the inner surface of the sleeve body 210. In other implementations, the inner surface of the sleeve body 210 may be provided with at least one indentation that runs along at least a portion of the longitudinal length of the sleeve 210. Such structures may appear as recessed features that appear as depressions on the inner surface of the sleeve body 210. In further implementations, a combination of projections and indentations may be provided along at least a portion of the longitudinal length of the sleeve body 210.

In certain implementations, raised features (e.g., projections) on the inner surface of the sleeve body 210 may additionally prevent axial rotation of the catheter body 210 when moving within the primary lumen 215. Such projections may mate with a groove on the catheter body 210 such that when the access sleeve 200 is attached to the catheter body 210, the projections on the inner surface of the sleeve body 210 engage with a corresponding groove on the catheter body 210 thereby preventing axial rotation of the medical device 100 as it moves within the access sleeve 200.

The access sleeve 200 may be used on its own (i.e., without the need of a guidewire) to maintain access to the vessel 320 when the pump 100 is retrieved or repositioned. In certain instances, more space in the vessel 320 may be necessary for other medical devices and so a guidewire may be used in conjunction with the access sleeve 200, after which the access sleeve 200 may be removed such that only the guidewire remains to maintain access to the vessel 320. The guidewire is inserted into the peripheral lumen 216 in the access sleeve 200 after the access sleeve has been attached to the catheter body 120. As with the primary lumen 215, the diameter of the peripheral lumen 216 is such that it establishes a clearance fit or an interference fit with a guidewire while allowing longitudinal movement of the guidewire with respect to the access sleeve 200. This prevents the ingestion of fluid in the peripheral lumen 216 which may coagulate and block the peripheral lumen. Alternatively, the access sleeve 200 may be pre-loaded with the guidewire in the peripheral lumen 216 prior to attaching the access sleeve 200 to the catheter body 120. Such a guidewire may provide additional mechanical strength to the access sleeve when pre-loaded. The peripheral lumen 216 terminates in the tip 240 at lateral opening 217, as shown in FIG. 5.

In certain embodiments, a guidewire lumen stylet may be inserted into the peripheral lumen 216 to plug it until the physician is ready to use the peripheral lumen 216 for the passage of a guidewire. Such a stylet will prevent blood from escaping. The stylet would have a clearance fit with the peripheral lumen 216 and does not protrude out past the outer surface of the distal end of the access sleeve (e.g., the stylet does not protrude past the lateral opening 217 in the tip 240). This would prevent the stylet from snagging tissue as the access sleeve 200 is positioned in the vasculature of the patient. In some implementations, the access sleeve 200 may be fabricated without a peripheral lumen 216.

In certain implementations, the sleeve body 210 may include integral support structures to increase the hold force of the access sleeve 200. Such support structures may also improve the overall rigidity of the sleeve 200. According to some implementations, such support structures may take the form of superelastic wires that are arranged longitudinally along the length of the sleeve body 210. In certain implementations, nitinol wires are used. Such support structures are incorporated within the sleeve body 210 during fabrication of the access sleeve 200.

Figure 6:
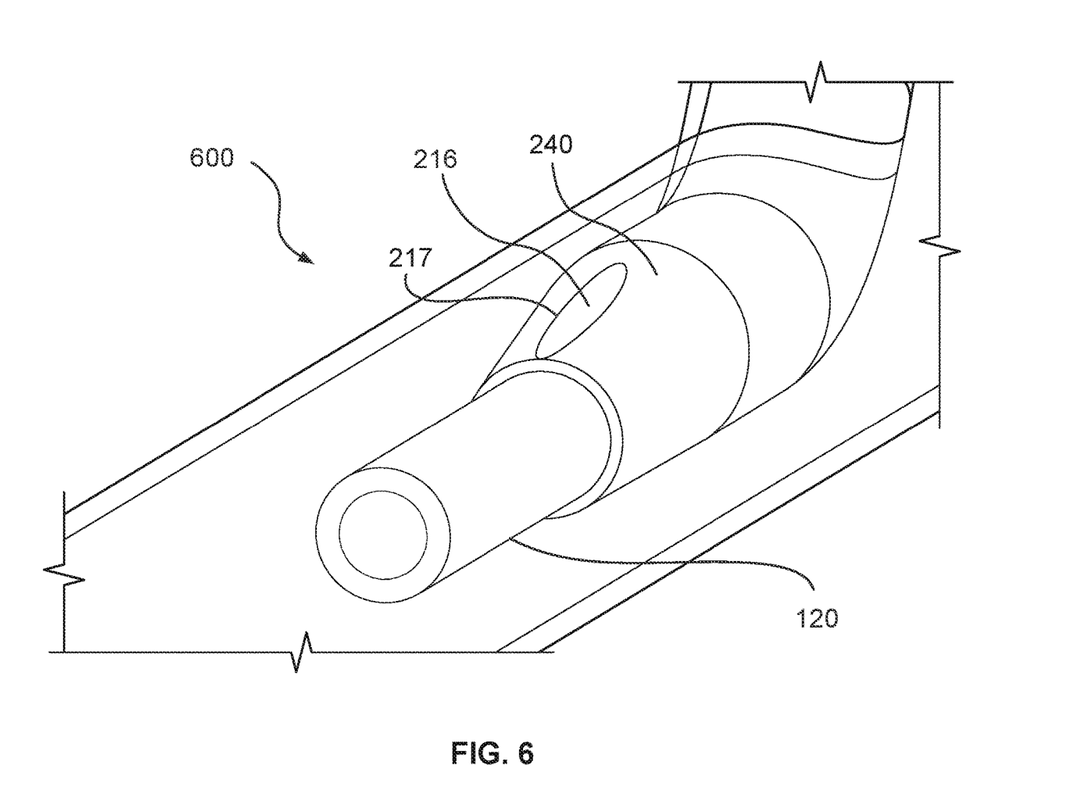
FIG. 6 shows an isometric view of a distal portion of the access sleeve of FIG. 2 attached to the medical device of FIG. 1.

FIG. 6 illustrates the atraumatic tip 240 attached to the access sleeve 200. With reference to FIGS. 2 and 6, the tip 240 is attached to the distal end 220 of the sleeve body 210 and has an internal lumen 242 and an open distal end 245 that is attached to the distal end 220 of the sleeve body 210. The proximal end 244 of the tip 240 is coupled to the distal end 220 of the sleeve body 210 such that lumens 215 and 242 are seamlessly in communication with each other. This allows for easy passage of the medical device 100 within the access sleeve 200. The inner surface of the tip 240 is slightly tapered such that the inner diameter is larger at the proximal end 244 than at the distal end 245 of the tip 240. This creates a slight inference fit with the medical device 100. This slight inference of the distal tip 240 with the medical device 100 helps seal any fluid or blood from entering the opening at the distal end 245 and hence the lumen 215. The outer surface of the tip 240 is also tapered towards the distal end 245 such that the outer diameter is larger at the proximal end 244 than at the distal end 245. The peripheral lumen 216 terminates in the tip 240 at lateral opening 217, as shown in FIG. 5. The distal end 244 of the tip 240 terminates at a leading edge 246. The outer diameter of the leading edge 246 has a radius to facilitate smooth insertion of the access sleeve 200 into the vasculature 320 of a patient. The tip 240 is highly resilient and will not exhibit permanent deformation (such as flaring or splitting). In certain implementations, the tip 240 comprises the same flexible material as the sleeve body 210. Further, the tapered surface of the tip 240 results in thinning of the walls of the tip 240 towards the distal end 245. This adds flexibility to the tip 240 and allows for less traumatic retrieval of an oversized medical device during removal from the vasculature of a patient.

In some implementations, the proximal end 230 of the access sleeve 200 may be coupled to a hub 250. The hub 250 has an internal conduit 252 that is in fluid communication with the primary lumen 215 of the access sleeve 200 when the hub assembly 250 is coupled to the sleeve body 210. The internal conduit 252 has a diameter 256. In certain implementations, the hub 250 has a passageway 254 which aligns with the peripheral lumen 216 when the access sleeve 200 is connected to the hub 250. The passageway 254 provides the user with a defined entryway for insertion of a guidewire into the peripheral lumen 216 after the access sleeve 200 is inserted into the vasculature 320 of a patient. In certain implementations, the hub 250 may also have an opening or a slit (not shown) that allows for the passage of a medical device 100 that has a diameter larger than the diameter 256 of the conduit 252. In other implementations the proximal end of the hub 250 may be configured to mate with the handle 110 of the medical device 100. The hub 250 may also have attachment features (e.g., wings or suture holes) that allow the access sleeve 200 to be secured to a patient. In certain implementations the hub may facilitate grip for the user of the access sleeve 200 over the medical device 100. In other implementations, the hub may also contain a hemostasis valve. The hub and the hemostasis valve may contain a slit or equivalent lateral opening that would facilitate attachment of the access sleeve (coupled to the hub) to the medical device.

The hub 250 may comprise a rigid material. The rigid material is a polyethylene or polyurethane material with an elastic modulus of about 40 ksi. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

Figure 7:
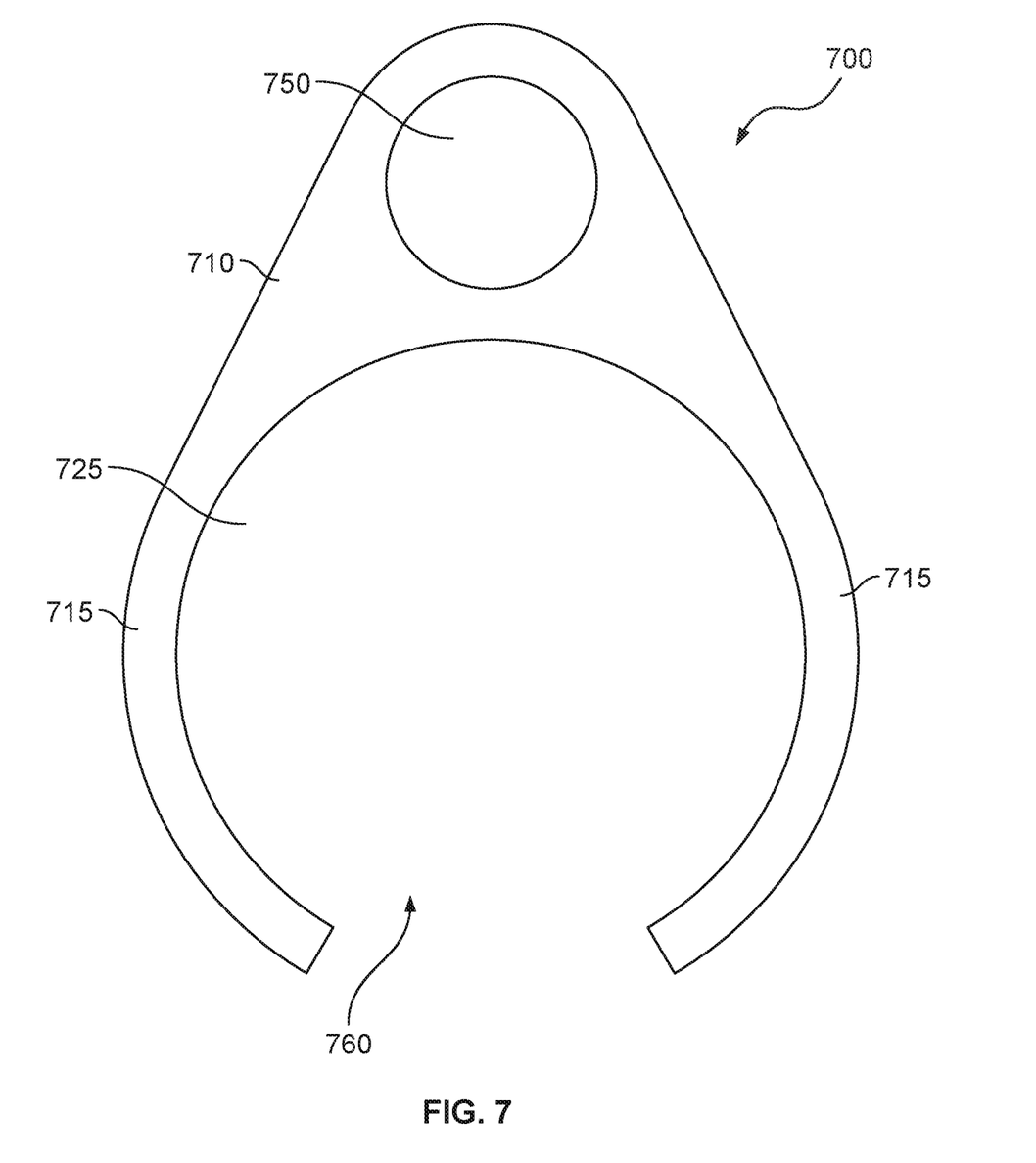
FIG. 7 shows a transverse cross section of a second embodiment of the illustrative access sleeve of FIG. 2.
Figure 8:
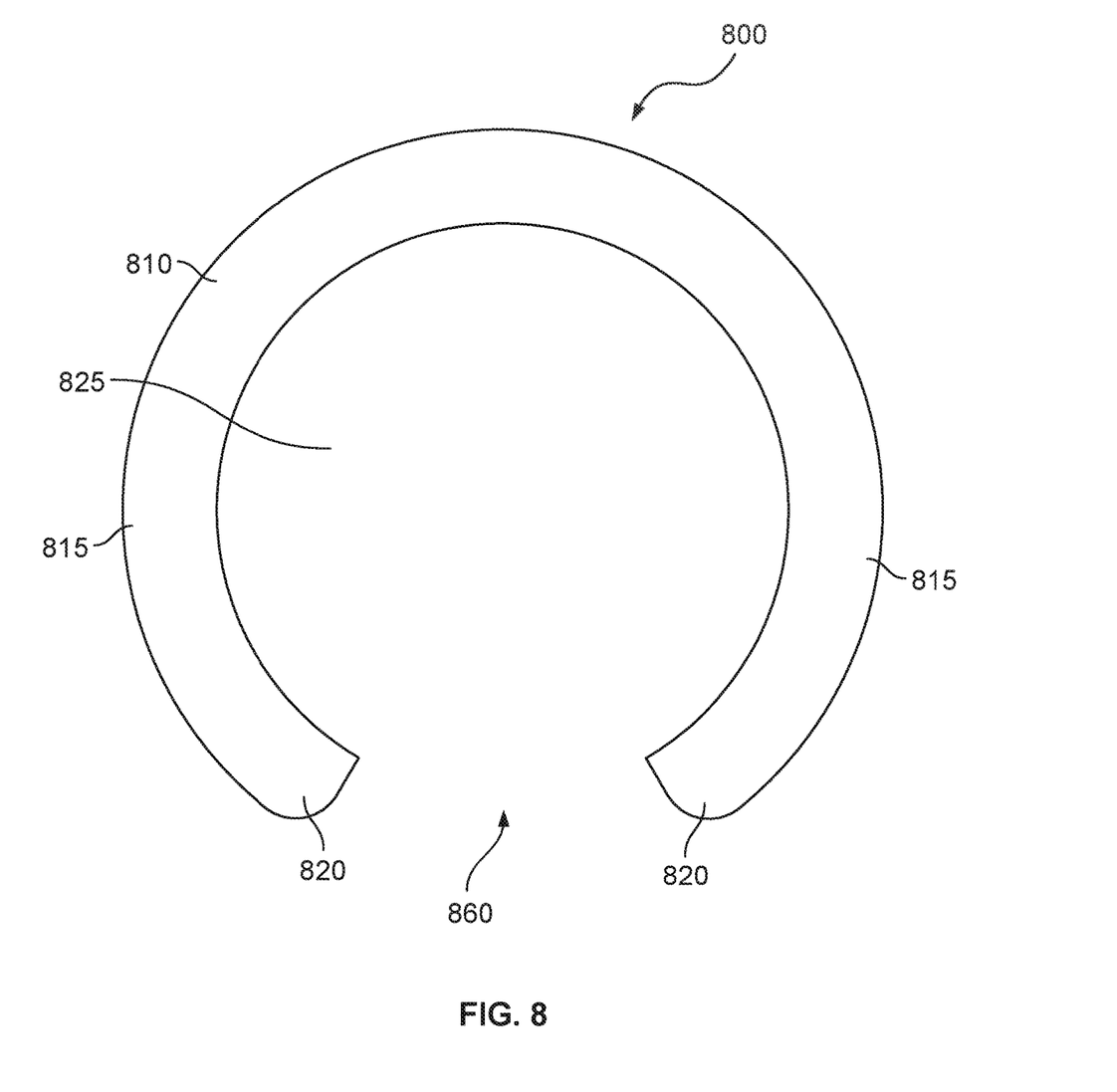
FIG. 8 shows a transverse cross section of a third embodiment of the illustrative access sleeve of FIG. 2.
Figure 9:
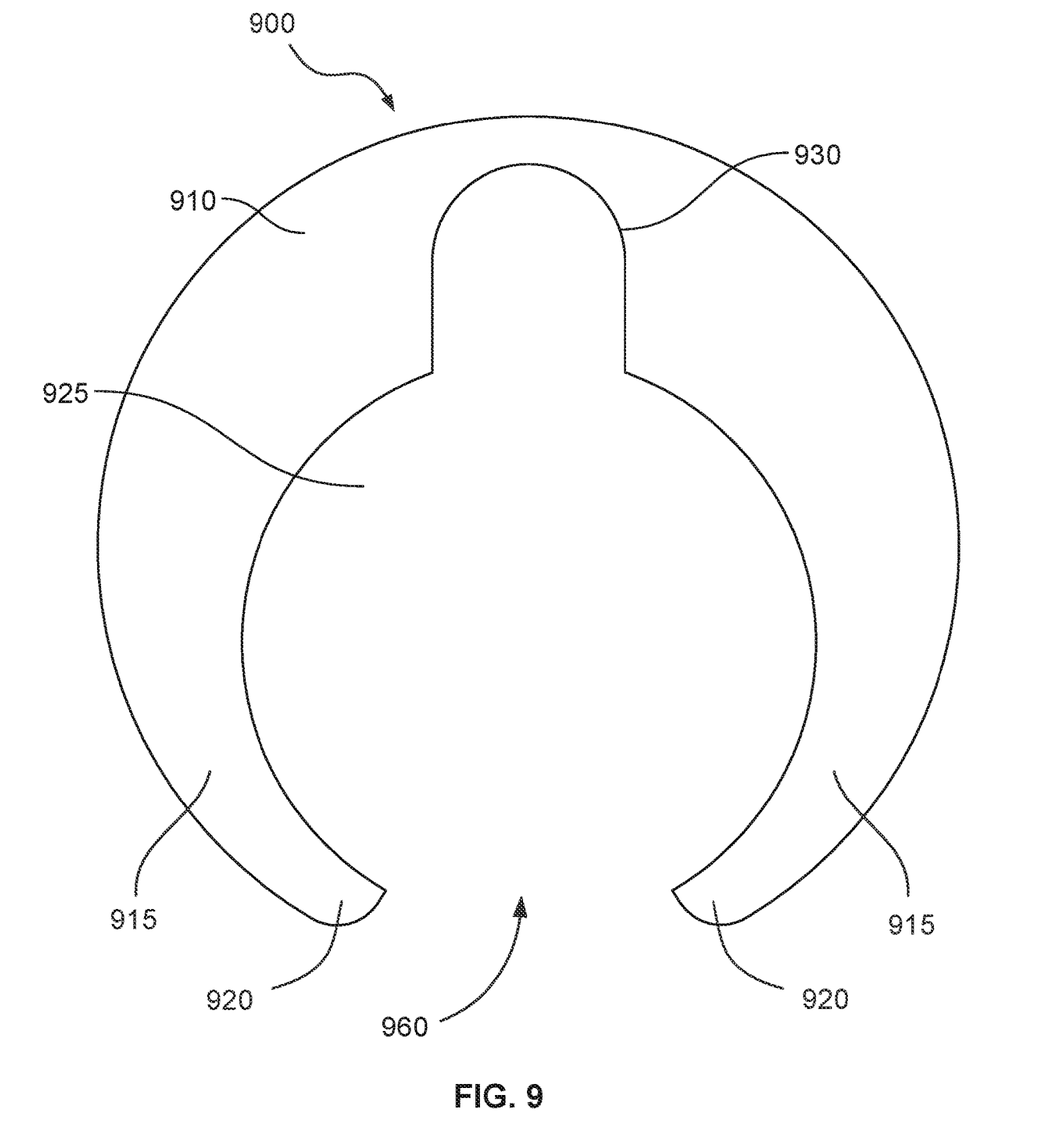
FIG. 9 shows a transverse cross section of a fourth embodiment of the illustrative access sleeve of FIG. 2.

Alternative implementations of the present disclosure will not be detailed with respect to FIGS. 7 to 9. FIG. 7 illustrates a cross section of an alternate access sleeve 700 according to certain implementations. Access sleeve 700 contains similar features to access sleeve 200 as illustrated in FIG. 2. Access sleeve 700 comprises a sleeve body 710 having a primary lumen 725 for passing of a medical device, such as the percutaneous pump 100, for example, and a peripheral lumen 750 for passage of a guidewire. Instead of a slit, access sleeve 700 contains an opening 760 that connects the primary lumen 725 to the outer surface of the sleeve body 710, thereby allowing for in-line and maintained attachment to a medical device. The access sleeve 700 comprises arms 715 that define the primary lumen 725 and the opening 760. As with access sleeve 200, the sleeve body 710 is also made of flexible elastic material such that the arms 715 are able to flex open and return to their original shape to allow attachment to a medical device. As the opening 760 is larger than the slit 260 in FIG. 2, attachment of the access sleeve 700 to a medical device is easier and has a clip-on effect due to the flexibility of the arms 715. The clip-on effect ensures that no space develops between the inner surface of the primary lumen 725 and the medical device. This prevents the flow of blood between the access sleeve 700 and the medical device which may lead to coagulation and blocking of the primary lumen 725.

FIG. 8 shows a cross section of a further alternate access sleeve 800 according to certain implementations. Access sleeve 800 comprises sleeve body 810 having a lumen 825 for passage of a medical device, and an opening 860 that connects the lumen 825 to the outer surface of the sleeve body 810. This configuration allows for the in-line attachment of the sleeve body 810 to the medical device. The lumen 825 and opening 860 are defined by arms 815 that span the length of the access sleeve 800. The arms 815 have rounded edges 820 to help facilitate smooth attachment to the medical device, and minimize trauma to the vasculature during insertion. Unlike the forgoing implementations, the access sleeve 800 does not contain a peripheral lumen for a guidewire. Instead, the diameter of the lumen 825 is selected such that the access sleeve 800 is able to accommodate both a medical device and a guidewire, if a guidewire is needed during use. Access sleeve 800 has a simple structure and is therefore easy to fabricate.

FIG. 9 shows a cross section of another alternate access sleeve 900 according to certain implementations. Access sleeve 900 comprises sleeve body 910 having a lumen 925 for passage of a medical device, and an opening 960 that connects the lumen 925 to the outer surface of the sleeve body 910. This configuration allows for the in-line attachment of the sleeve body 910 to the medical device. The access sleeve 900 also has a track or recess 930 that protrudes inwards from the surface of lumen 925 into to the sleeve body 910. When the access sleeve 900 is attached to a medical device, track or recess 930 forms a guided insertion path for a guidewire. The lumen 925 and opening 960 are defined by arms 915, each of which have rounded edges 920 to help facilitate smooth attachment to the medical device, and minimize trauma to the vasculature during insertion.

Figure 10:
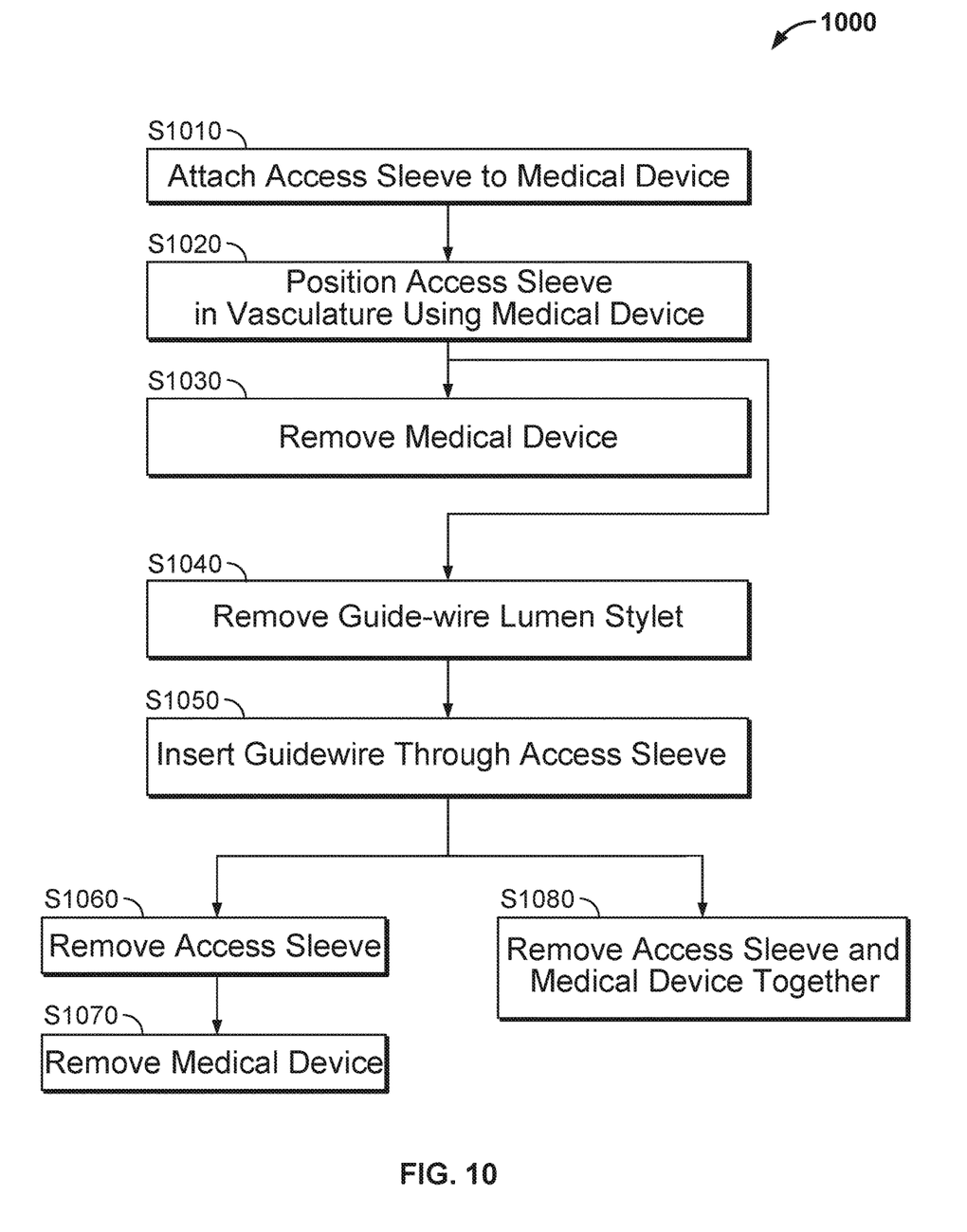
FIG. 10 shows an illustrative method for attaching a guidewire access sleeve of FIG. 2 to the medical device of FIG. 1.

FIG. 10 shows an illustrative method 1000 of using any of the aforementioned access sleeves 200, 700, 800 and 900, or any other suitable access sleeve. The method 1000 will be described in relation to access sleeve 200, but can be applied to any of access sleeve described herein. As has been discussed in the preceding sections, an access sleeve according to the present disclosure is used in conjunction with a medical device, such as a percutaneous heart pump 100. Such a medical device has a catheter body 120 and is inserted into the vasculature of a patient to perform a function at an access site. In so doing, a first portion of the indwelling catheter will be exterior to the vasculature while a second portion of the indwelling catheter will be positioned at the access site. Once the medical device has performed its function, it may be necessary to completely remove it from the vasculature, or reposition (or reload) a medical device while still maintaining access to the vasculature.

At step S1010, the distal portion 220 of the access sleeve 200 is attached to the first portion of the catheter body 120 by opening the slit 260 with the application of a separating force to the distal tip 220 of the sleeve body 210. The sleeve body 210 of the access sleeve 200 is the pushed onto the second portion of the catheter body 120 via slit 260 until the catheter body 120 is located in lumen 215 of the sleeve body 210. Once this occurs, the remaining length of the access sleeve 200 is attached to the second portion of the catheter body 120 until the entire sleeve body 210 co-axially encompasses the catheter body 120. This can be achieved by applying a longitudinal force on the proximal end 230 of the sleeve body 210. In this manner, the access sleeve 200 is attached in-line to the percutaneous pump 100 without having access to the end of the catheter 120, i.e., without having access to the pump head 130.

At step S1020, the access sleeve 200 is positioned in the vasculature of the patient by sliding it along the catheter body 120, and, in so doing, the access sleeve will be guided into the access site by the catheter body 120. The catheter body 120 effectively serves as a guide rail for longitudinally positioning the access sleeve 200 along the catheter body 120. In certain implementations, a guidewire may additionally be inserted into a peripheral lumen 216 of the access sleeve to gain access to the access site. The guidewire is inserted into the peripheral lumen 216 via a hub 250 located at the proximal end 230 of the access sleeve 200.

At step S1030, after positioning the access sleeve (and guidewire, if necessary) at the desired location within the vasculature of the patient, the percutaneous pump 100 is removed or repositioned as necessary. As previously mentioned, the diameter 218 of the lumen 215 may be smaller than that of the pump head 130. Thus, during removal or repositioning of the pump 100, the slit 260 allows for expansion of the access sleeve 200 and lumen 215 such that the pump head 130 is able to longitudinally move within the expanded lumen to be retrieved. After retrieval of the pump 100, the access to the access site is maintained by the access sleeve 200 (or the guidewire, if present, or both).

In certain implementations, prior to removing the medical device in step 1030, the guidewire lumen stylet is removed from the peripheral lumen 216 of the access sleeve 200 (step S1040). Once the guidewire lumen stylet is removed, a guidewire is inserted into the peripheral lumen 216 of the access sleeve 200, as shown in step S1050. Here the guidewire is inserted such that a distal portion of the guidewire extends beyond the access sleeve and into the vasculature of the patient. At the point, the access sleeve 200 is removed (step S1060), and, if necessary, the medical device 100 is removed (step S1070), thereby leaving just the guidewire to maintain access to the vasculature of the patient. In certain implementations, once the guidewire is positioned in the vasculature (step S1050), both the access sleeve 200 and the medical device 100 are removed together, leaving just the guidewire to maintain access to the vasculature of the patient (step S1080).

In view of the foregoing, the person of ordinary skill will appreciate that the present disclosure provides a means of maintain access to an arteriotomy of a patient during use of a repositioning sleeve and/or removal of an indwelling pump, without having access to the distal (indwelling) ends of these devices.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A vascular access sleeve comprising:
a sleeve body extending along a longitudinal axis of the access sleeve, the sleeve body having first and second open ends;
a hub attached to the second open end of the sleeve body, the hub having third and fourth open ends, and further including a hemostasis valve;
a first lumen extending along the longitudinal axis between the first and second open ends of the sleeve body, and further extending between the third and fourth open ends of the hub;
a second lumen extending parallel to the longitudinal axis between the first and second open ends of the sleeve body, the second lumen forming a track running alongside the first lumen;
a first lateral opening in the sleeve body, the hub, and the hemostasis valve, the first lateral opening extending from the first open end to the second open end of the sleeve body, and from the third open end to the fourth open end of the hub; and
a second lateral opening between the first lumen and the second lumen, the second lateral opening extending from the first open end to the second open end of the sleeve body,
wherein the first lateral opening is expandable and configured to enable attachment of the access sleeve to a medical device between a first end and a second end of the medical device such that the medical device becomes housed within the first lumen, and
wherein the first lateral opening and the second lateral opening are configured to enable attachment of the access sleeve to a guidewire between a first end and a second end of the guidewire such that the guidewire becomes housed within the second lumen.

2. The access sleeve of claim 1, wherein at least one edge of the first lateral opening is rounded.

3. The access sleeve of claim 1, wherein the first lateral opening extends linearly between the first and second open ends of the sleeve body and is parallel to the longitudinal axis of the first lumen of the sleeve body.

4. The access sleeve of claim 1, wherein the first lateral opening extends in a helical spiral between the first and second open ends of the sleeve body.

5. The access sleeve of claim 1, wherein the sleeve body comprises an inner surface having an irregular geometry configured to reduce contact between the sleeve body and the medical device.

6. The access sleeve of claim 5, wherein the inner surface comprises at least one recess extending between the first and second open ends of the sleeve body, the recess being different than the second lumen.

7. The access sleeve of claim 1, wherein the hub further comprises wings or suture holes configured to allow the hub to be secured to a patient.

8. The access sleeve of claim 1, further comprising a tip at the first open end of the sleeve body, the tip having an inner surface defining a tip lumen that extends between a proximal end and a distal end of the tip, the tip lumen being in fluid communication with the first lumen of the sleeve body.

9. The access sleeve of claim 8, wherein an outer diameter of the proximal end of the tip is larger than an outer diameter of the distal end of the tip such that the tip is tapered along its length.

10. The access sleeve of claim 8, wherein a diameter of the inner surface at the proximal end of the tip is larger than a diameter of the inner surface of the tip at the distal end of the tip.

11. The access sleeve of claim 8, wherein a diameter of the inner surface at the proximal end of the tip is equal to a diameter of the inner surface at the distal end of the tip.

12. The access sleeve of claim 8, wherein the sleeve body comprises a first material and the tip comprises a second material.

13. The access sleeve of claim 12, wherein the first material is substantially stiffer than the second material, and the second material is substantially more elastic than the first material.

14. The access sleeve of claim 12, wherein the first material comprises at least one of: high-density polyethylene (HDPE) material, a medium-density polyethylene (MDPE) material, a low-density polyethylene (LDPE) material, a polyether block amide (PEBA), a material with an elastic modulus of about 81-307 MPa, or a material with a yield strain of 20-30%.

15. The access sleeve of claim 12, wherein the second material comprises at least one of: ethylene-vinyl acetate (EVA), styrene-butadiene copolymer (SBC), synthetic rubber, an elastomer, an elastic material, a material with an elastic modulus of about 1.6 ksi, or a material with a yield strain in excess of 200%.

16. The access sleeve of claim 7, wherein the hub comprises at least one of: a high-density polyethylene (HDPE) material, a medium-density polyethylene (MDPE) material, a low-density polyethylene (LDPE) material, polyether ether ketone (PEEK), or a polyether block amide (PEBA).

17. An access system comprising:
a medical device configured for insertion into an arteriotomy of a patient, the medical device having a first end and a second end; and
an access sleeve having a sleeve body extending along a longitudinal axis, the sleeve body having first and second open ends;
a hub attached to the second open end of the sleeve body, the hub having third and fourth open ends, and further including a hemostasis valve;
a first lumen extending along the longitudinal axis between the first and second open ends of the sleeve body, and further extending between the third and fourth open ends of the hub;
a second lumen extending parallel to the longitudinal axis between the first and second open ends of the sleeve body, the second lumen being forming a track running alongside the first lumen;

a first lateral opening in the sleeve body, the hub, and the hemostasis valve, the first lateral opening extending from the first open end to the second open end of the sleeve body, and from the third open end to the fourth open end of the hub; and a second lateral opening between the first lumen and the second lumen, the second lateral opening extending from the first open end to the second open end of the sleeve body, wherein the first lateral opening of the access sleeve is expandable and configured to enable attachment of the access sleeve to the medical device between the first end and the second end of the medical device such that at least a portion of the medical device becomes housed within the first lumen, and wherein the first lateral opening and the second lateral opening are configured to enable attachment of the access sleeve to a guidewire between a first end and a second end of the guidewire such that the guidewire becomes housed within the second lumen.

18. The access system of claim 17, wherein the sleeve body has a cross-sectional shape that is substantially C-shaped.

19. The access system of claim 17, wherein the medical device includes a catheter, and wherein the first lateral opening is configured to enable attachment of the access sleeve to the catheter.

20. The access system of claim 19, wherein the first lumen of the sleeve body is configured to enable the access sleeve to be advanced distally along the catheter and into an arteriotomy of a patient while attached to the catheter.

21. The access system of claim 17, wherein at least one edge of the first lateral opening is rounded.

22. The access system of claim 17, wherein the sleeve body comprises an inner surface having an irregular geometry configured to reduce contact between the sleeve body and the medical device.

23. The access system of claim 22, wherein the inner surface comprises at least one recess extending between the first and second open ends of the sleeve body, the recess being different than the second lumen.

24. The access system of claim 17, wherein the hub further comprises wings or suture holes configured to allow the hub to be secured to a patient.

* * * * *